United States Patent [19]

DeSimone

[11] 4,156,690
[45] May 29, 1979

[54] METHOD FOR PREPARING UNSATURATED NITRILES

[75] Inventor: Robert S. DeSimone, Middletown, N.Y.

[73] Assignee: Polak's Frutal Works, Inc., Middletown, N.Y.

[21] Appl. No.: 746,573

[22] Filed: Dec. 1, 1976

[30] Foreign Application Priority Data

Dec. 11, 1975 [GB] United Kingdom ............... 50829/75

[51] Int. Cl.$^2$ ........................................... C07C 120/00
[52] U.S. Cl. ................................ 260/464; 260/465.9; 252/522
[58] Field of Search ............................. 260/465.9, 464; 252/522

[56] References Cited

U.S. PATENT DOCUMENTS

| | | | |
|---|---|---|---|
| Re. 27,332 | 4/1972 | Somerville et al. | 252/522 |
| 2,333,782 | 11/1943 | Hansley | 260/465.9 |
| 2,375,016 | 5/1945 | Marple et al. | 260/465.9 |
| 3,030,408 | 4/1962 | Inman et al. | 260/465.4 X |
| 3,157,660 | 11/1964 | Stilz et al. | 260/465.9 |
| 3,267,132 | 8/1966 | Newsom | 260/465.9 |
| 3,531,510 | 9/1970 | Blumenthal | 252/522 X |
| 3,553,110 | 1/1971 | Mitchell et al. | 252/522 |
| 3,719,701 | 3/1973 | Bach | 260/465.9 |
| 3,766,239 | 10/1973 | Colleuille et al. | 260/465.9 |
| 3,842,128 | 10/1974 | Schwarz et al. | 260/465.9 |
| 3,960,923 | 6/1976 | DeSimone | 260/465.9 |
| 3,992,432 | 11/1976 | Napier et al. | 260/465.1 |

FOREIGN PATENT DOCUMENTS

2135666 1/1973 Fed. Rep. of Germany ........... 260/464
2333265 1/1974 Fed. Rep. of Germany ........ 260/465.9

OTHER PUBLICATIONS

C.A., 54-1282c, Sarycheva et al., (1960).
C.A., 77-126084p, Arpe et al., (1972).
Arpe, et al., Angew. Chem., Int. Ed. Engl. (1972) p. 722.
Levine, et al., J.A.C.S., 68 (1946), pp. 760-761.
Hauser, et al., J. Org. Chem., 15 (1950), pp. 359-366.

*Primary Examiner*—Joseph Paul Brust
*Attorney, Agent, or Firm*—William S. Alexander

[57] ABSTRACT

Alpha, beta-dialkyl conjugated nitriles are disclosed which have interesting perfumistic qualities. These materials have the general structural formula

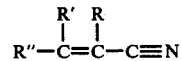

where R is an aliphatic hydrocarbon radical of about 1 to 15 carbon atoms having no unsaturation in conjugated relationship with either the nitrile unsaturation or the alpha, beta-olefinic unsaturation, and R' and R" are the same or different aliphatic hydrocarbon radicals meeting the description of R, or R' and R", taken together, form a cycloaliphatic radical having about 6 to 15 carbon atoms. They are produced by the reaction of the appropriate aliphatic nitrile and ketone under the influence of a basic catalyst.

9 Claims, No Drawings

METHOD FOR PREPARING UNSATURATED NITRILES

This invention relates to a novel series of conjugated, unsaturated aliphatic nitriles and to a process for the preparation thereof. It also relates to perfume compositions wherein these novel compounds are included as olfactory components.

Modern trends in perfumery have increasingly demanded that the perfumer expand his palette beyond the traditionally employed natural extracts and oils to the use of chemical synthetics. This need for aroma synthetics derives both from the competitive stimulus for new fragrance effects on the marketplace and the increasing cost of the standard perfumery raw materials for which inexpensive, chemically derived substitutes are becoming increasingly important. It has been found possible, through the use of synthetic aroma chemicals, to produce new odor effects in the perfumery art and, more importantly, to prepare these at prices more attractive and less subject to fluctuation than those of natural derivatives.

Another requirement of modern perfumery is fragrance stability, since perfumes are increasingly being incorporated into household, cosmetic, soap, detergent and industrial cleanser products to enhance their aesthetic aspect. With the aforementioned products it has become imperative, for reasons of consumer acceptance, to design perfumes having greater stability to heat, light, oxidation and hydrolytic effects, which result from either the formulation of the product, or due to the storage requirements and usage conditions for such a product.

It is the objective of this invention to provide a novel series of perfumery compounds which exhibit the stability required for the various applications mentioned hereinabove while also exhibiting pleasing aroma characteristics. It is also an objective of this invention to provide such a series of perfumery compounds having odor characteristics making them useful in a wide variety of perfume applications.

It is a further objective of this invention to provide a novel synthetic method of preparing hitherto unknown unsaturated conjugated nitriles via a relatively simple and inexpensive route. Specifically, the novel compounds of this invention are alpha, beta, dialkyl-substituted conjugated aliphatic nitriles having the following general structural formula:

$$R''-C(R')=C(R)-C\equiv N$$

where R is an aliphatic hydrocarbon radical of about 1 to 15 carbon atoms having no unsaturation in conjugated relationship with either the nitrile unsaturation or the alpha, beta-olefinic unsaturation, and R' and R" are the same or different aliphatic hydrocarbon radicals meeting the description of R, or R' and R", taken together, form a cycloaliphatic radical having about 6 to 15 carbon atoms. Exemplary, but by no means all inclusive of, alpha, beta-dialkyl conjugated nitriles within the scope of the above formula are, e.g., 2,3-dimethyl-2-nonenenitrile, 2,3-dimethyl-2-octene nitrile, 2-ethyl-3-methyl-2-nonene nitrile, 2-ethyl-3-methyl-2-octene nitrile, 2-ethyl-3,7-dimethyl-2,6-octadiene nitrile, 2,3,7-trimethyl-2,6-octadiene nitrile and 2-cyclohexylidene butyronitrile. Other exemplary nitriles are:

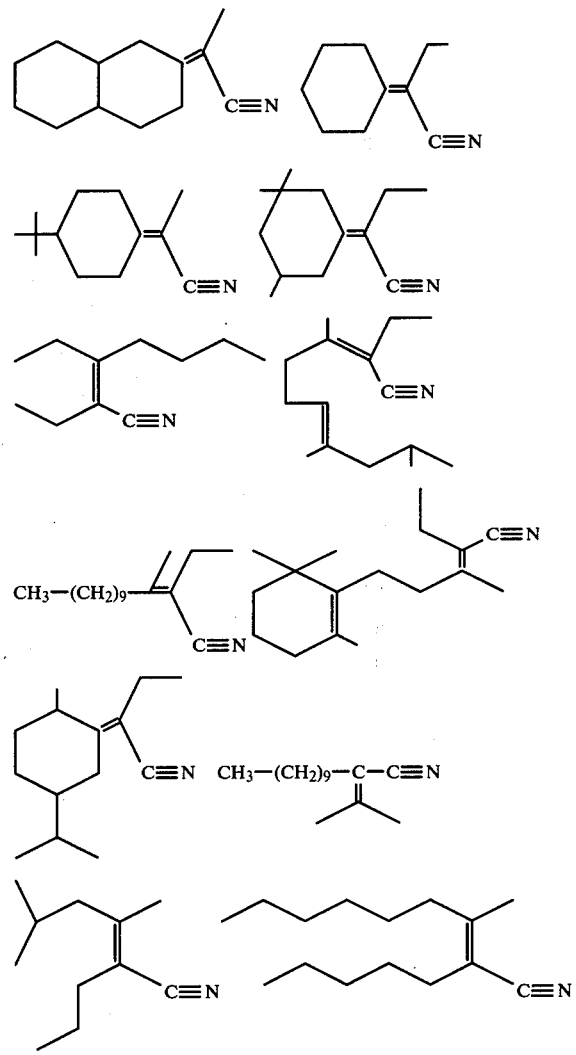

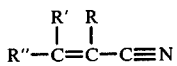
CH₃—(CH₂)₉—

The novel α,β-dialkyl conjugated aliphatic nitriles of this invention have been found to be useful as perfumery ingredients exhibiting a variety of commercially useful fragrance notes. Some members of the class have a jasmine-like fragrance, others have other floral notes, while still others exhibit a woody, cinnamic fragrance. They are useful alone, mixed with each other, or, more normally, mixed with other perfumery compounds in about 0.1 to 30% concentration to form a perfume, when mixed with a suitable carrier.

The nitriles of this invention have been found to possess a high degree of stability to acidic or basic media, oxidative conditions, and thermal effects relative to many compounds widely used in perfumery, such as allylic alcohols or esters, aldehydes, epoxides, and the like. Moreover, in most cases, the α,β-dialkyl nitriles of this invention surpass the chemical stability of the corresponding alpha unsubstituted nitriles. The contrast in stability of the unsaturated conjugated nitriles, in general, over that of the corresponding aldehydes, is well exemplified by that of geranonitrile (3,7-dimethyl-2,6-octadiene nitrile) in comparison to citral (3,7-dimethyl-2,6-octadienal), the latter of which is known to be much less stable when employed in perfumes for soaps, containing alkaline carboxylate salts of fatty acids (see Arctander "Perfume and Flavor Chemicals", published by Steffen Arctander, P.O. Box 114, Elizabeth, N.J. 1969). We have now found the analogous alpha-alkyl nitriles of this invention, namely α-methyl geranonitrile (2,3,7-trimethyl-2,6-octadiene nitrile) and α-ethyl geranonitrile (2-ethyl-3,7-dimethyl-2,6-octadiene nitrile) to be far more stable to the combined action of heat and air than the alpha-unsubstituted homologue, geranonitrile.

In U.S. Pat. No. 3,655,722 a method is described whereby geranonitrile and other olefin isomers are prepared as a mixture by the condensation of 6-methyl-2-keto-hept-5-ene with cyano acetic acid in the presence of an amine or an acid addition salt of an amine. The isomeric mixture of 7-methyl-2,6-octadiene nitriles thus produced is formed only in poor yield (22% conversion) and the starting material, cyano acetic acid, is quite expensive, especially when one considers its high usage in relation to product formed in the reaction - almost five moles are consumed for only one mole of product formed. The corresponding condensation to form alpha-alkyl conjugated nitriles by use of an alkyl substituted cyano acetic acid or ester in reaction with a ketone, such as 6-methyl-2-keto-hept-5-ene, does not proceed to give useful yields of product because of the steric hinderance of such a combination. To our knowledge, this analogous condensation has not been reported in the literature.

In my earlier U.S. Pat. No. 3,960,923 there is described a method for the condensation of acetonitrile with ketones over various bases to form conjugated nitriles. In a similar manner, but by a different method, Arpe and Leupold, Angew. Chem. Internat. Ed. 11, 722 (1972), German Offenlegungsschrift No. 2,135,666, published Jan. 25, 1973, describes the reaction of ketones, such as cyclohexanone with acetonitrile, in the presence of an alkali metal alcoholate of a high boiling alcohol.

In accordance with this invention, a ketone is reacted with higher alkyl nitriles, in the presence of a basic catalyst, in an aldol-type condensation to give a novel class of α,β-dialkyl conjugated aliphatic nitriles (trialkyl-substituted acrylonitriles) having carbon skeletons not readily available through classicial synthetic routes. The use of simple base reagents to effect the condensation of the α-carbanions of higher nitriles is known to date in the literature and has not heretofore been employed to perform aldol condensations with ketones to give the products of this invention, the trialkyl substituted acrylonitriles.

The reaction can be described as follows:

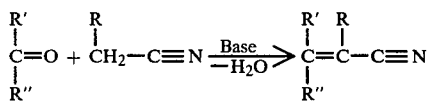

where R, R' and R" are as hereinabove defined.

The bases employed are selected from the group of alkali or alkali earth hydroxides, metal alcoholates and quaternary ammonium hydroxides, either used alone or in combination. When calcium hydroxide is used, a phase-transfer agent, such as crown ether or quaternary ammonium chloride or hydroxide, must also be employed.

The nitrile α-carbanion attacks the carbonyl carbon to form an intermediate aldol which dehydrates to form the trialkyl substituted acrylonitrile. Examples of some, but by no means all, ketones which can be used include 6-methyl-5-hepten-2-one, 3,6-dimethyl-hepten-2-one, 7-methyl-6-octen-3-one, 2-octanone, 3-heptanone, cyclohexanone, 4-methyl cyclohexanone, 4-tert-butyl cyclohexanone, 6,9-dimethyl-5-decen-2-one, cycloheptanone, 2-decanone and 2-dodecanone. Other useful ketones are the following:

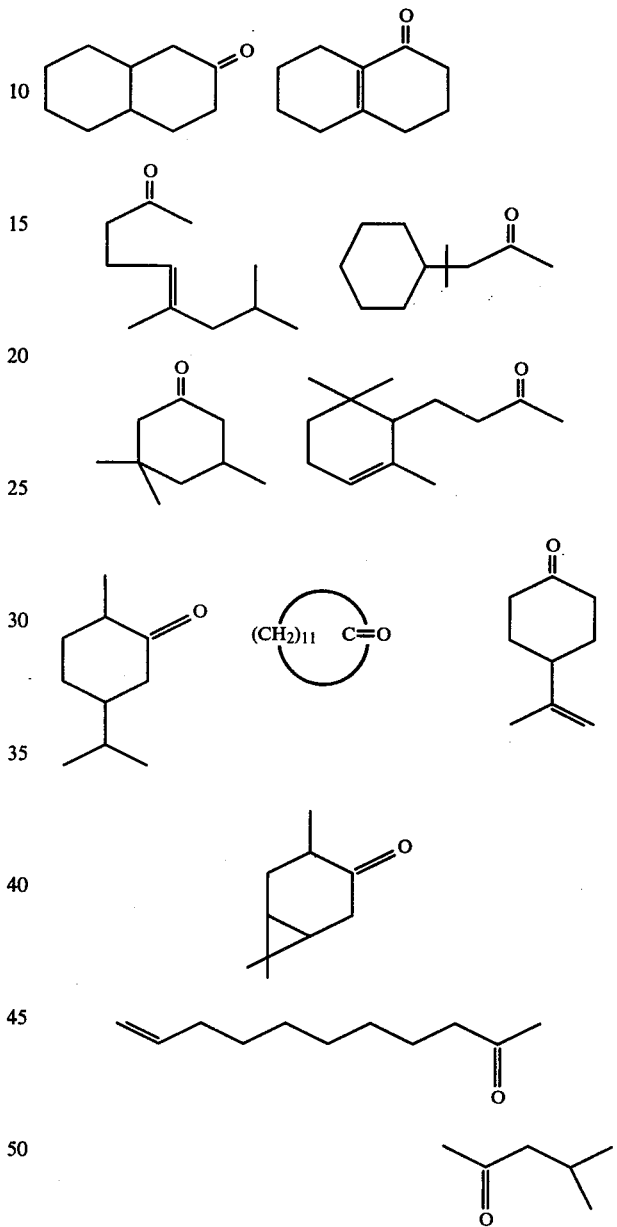

The reaction proceeds with stoichiometric ratios of ketone and alkylnitrile. An excess of either reagent can be used, however, if desired, to aid the reaction to proceed to the desired extent or to provide suitable reaction conditions for the combination of reactants employed. The amount of alkali can be within the range from about 0.01 to about 10 moles per mole of ketone. Preferably, the amount of base is within the range from about 0.1 to about 5 moles per mole of ketone. Normally, there is no need to use more than one mole of alkali per mole of ketone.

It is advantageous to have the base in solution, at least to some extent, in which event the reaction rate is increased. An organic solvent for the base, e.g., dimethyl sulfoxide or m-pyrrole, can consequently be included in the reaction mixture when a relatively insoluble base such as barium hydroxide, is employed. Such solvents activate the base and it is more effective in their presence.

It has also been found that phase-transfer catalysts such as crown ethers (e.g., cyclic ethylene oxide oligomers), quaternary ammonium halides or phosphonium salts, can greatly accelerate the action of relatively insoluble, and therefore, slowacting bases. Hydroxylic bases, which are otherwise inert, such as calcium hydroxide, can thus be made to function quite satisfactorily. This is a critical feature when one performs reactions employing the higher alkyl nitriles, which have a non-polar or lipophilic solvent character, in contradistinction to acetonitrile, which has a strong polar solvent action for many of the hydroxylic bases used in U.S. Pat. No. 3,960,923.

It is not, however, necessary to add an inert solvent. The alkynitrile can serve not only as a reagent but also as a solvent, and for this purpose it can be used in excess. The presence of the excess alkylnitrile is additionally beneficial in that it can serve as a water trapping agent. Water generated during the course of reaction is captured through a base-catalyzed hydrolysis of the alkylnitrile to form the corresponding amide.

Other water trapping agents, such as molecular sieves or metal oxides such as calcium oxide, can also be used. Water can also be removed by using an external inert diluent which need not be a solvent for the base, but which forms an azeotrope with water. Such water can be azeotropically removed, caught under reflux in a water trap, and prevented from returning to the reaction mixture. Suitable azeotropic solvents include toluene, benzene and xylene.

The reaction takes place at room temperature, or even slightly below. It can be, however, accelerated by increasing the temperature. The maximum temperature is imposed by the temperature of decomposition of the $\alpha,\beta$-unsaturated nitrile reaction product. Usually, the reaction temperature need not exceed about 200° C., and can range to 20° C. or below. The preferred temperature is within the range from 50° C. to about 125° C.

The reaction can be carried out at atmospheric pressure. If, however, a volatile solvent is used, at a reaction temperature at or near its atmospheric boiling point, it may be desirable to conduct the reaction in a closed reactor, such as an autoclave, in order to maintain the solvent in the liquid phase in the reaction mixture, or under reflux.

The reaction can be completed within about 30 minutes, but in some cases, an extended time, to as much as 120 hours or more, is needed. This is without disadvantage, since the $\alpha,\beta$-unsaturated nitrile is the final product, and disproportionation or transmutation of this product into other materials does not appear to take place. The reaction time can be kept short by increasing the reaction temperature, improving the efficiency of the agitation, and using a concentration reaction mixture.

At the completion of the reaction, the reaction mixture can be treated with acid to neutralize the base. The reaction product can then be dissolved in an organic solvent for the reaction product, such as benzene, which is not miscible with the aqueous phase, and in this way the aqueous phase is separated from the organic phase containing the reaction product. The aqueous phase can be extracted several times with the solvent, in order to maximize the recovery.

Alternatively, the reaction mixture can be washed with water to remove the majority of base and any water-soluble by-products. The remaining organic phase is then washed with a dilute aqueous acid solution to ensure removal of all remaining traces of base. The same result can be achieved through filtration of a crude reaction mixture to remove the majority of base and amide, again using an acid wash to remove any remaining traces of base. It has been found advantageous with many of the nitriles of this invention to perform the workup in such a manner as to use an acid wash to aid extraction of amide and heterocyclic amine by-products. strong acids, such as sulfuric and hydrochloric in aqueous solution, have been found to make effective wash solutions. It has also been found advantageous to use a strong base wash to remove traces of free fatty acid by-products, corresponding in carbon number to the $\alpha,\beta$-dialkyl conjugated aliphatic nitrile product, which may have been liberated by the preceding acid wash. It has been found that strong bases, such as potassium and sodium hydroxide in aqueous solution, serve as efficient wash solutions for this purpose.

The combined organic phases can then be concentrated to remove the solvent, preferably at reduced pressure and a low temperature, and then distilled at reduced pressure to separate the unreacted starting materials, including starting ketone and alkylnitrile, from the $\alpha,\beta$-dialkyl conjugated aliphatic nitrile. The unsaturated nitrile product can exist as a cis, trans mixture, where stereoisomers are possible, but separation of cis, trans isomers is not necessary.

The following examples represent preferred embodiments of the invention but are intended to be illustrative only and not limiting.

EXAMPLE 1

3,7-Dimethyl-2-Ethyl-2,6-Octadiene Nitrile

Methyl heptenenone (6-methyl-heptene-5-one-2) (25.2 g.) was combined with 138 g. of butyronitrile and 12.2 g. of KOH was then added. The mixture was heated to reflux with stirring at 118° C. for a total of 15 hours under $N_2$. Crude butyronitrile was recovered by distillation at between 85° and 141° C. pot temperature and 81° to 89° C. head temperature using a short path still head at <300 mm. Hg. The pot contents were then cooled to 100° C., 100 ml. of $H_2O$ was added, and the mixture was stirred one hour. Hydrochloric acid, 10%, 100 cc. was then added with stirring along with 100 ml. of benzene. Another 200 ml. of 4% HCl were added with stirring and the oil phase separated. The aqueous phase was extracted with one 15 ml. portion of toluene and then with 10 ml. portions five times. The combined oil phases were distilled at 208 to 213 mm. Hg, 68° to 167° C. pot temperature and 55° to 118° C. head temperature to remove solvent on an 18 inch Vigreaux column. The product nitrile distilled at 118° to 135° C. head temperature and 142° to 205° C. pot temperature at 17 mm. Hg. The fraction containing the product nitrile was taken up in hexane and washed with water three times to remove crystals of butyronitrile. The washed nitrile was redistilled to give the product as a mixture of cistrans isomers in 16% conversion yield. The product was interpreted by some perfumers to have a jasmin or immortelle-type fragrance.

EXAMPLE 2

2,3-Dimethyl-2-None Nitrile

Into a one-liter flask equipped with mechanical stirrer, heating mantle, thermometer, condensor, and static nitrogen head was charged 64 g. of octanone and 275 g. of propionitrile. KOH (32.9 g.) was then added and the mixture heated to reflux (95° C.) for 19 hours. After cooling, 35% hydrochloric acid was added to pH 6 and excess propionitrile recovered by distillation at between 120 and 535 mm. Hg, 60° to 73° C. head temperature and 68° to 79° C. pot temperature. The pot contents were cooled, 90 ml. of hexane were added and the slurry washed once with 150 ml. of water and two 50 ml. portions of water. After distillative recovery of hexane, the remaining oil was flash distilled at 30 mm. Hg to recover unreacted ketone and then at 8 mm. Hg, pot temperature was raised to 192° C. and head temperature to 112° C. to recover product. The product was fractionally distilled on an 18 inch micro Vigreaux column equipped with reflux head:

Charge:
52.5 g. crude product
3 g. Primol 355
0.1 g. Ionox 220

Parameters:
90° to 99° C. head temperature
92° to 165° C. pot temperature

The product, obtained in 47.8% direct yield, 53.7% true yield, was interpreted by some perfumers to have a jasmine, floral nitrile-type odor.

EXAMPLE 3

2,3,7-Trimethyl-2,6-Octadiene Nitrile

Into a two-liter three-necked flask equipped with mechanical stirrer, heating mantle, thermometer, condensor and drying tube was added in succession 126 g. of methyl heptenone, 550 g. of propionitrile and 65.9 g. of 85% potassium hydroxide. The mixture was heated to reflux (79° to 82° C.) for a total of 20.5 hours whereupon the product was cooled and allowed to stand overnight. Next, 100 cc. of concentrated HCl was added with stirring and cooling until pH 6 was obtained. Excess propionitrile (348 g.) was recovered at between 270 and 560 mm. Hg, 53° to 75° C. head temperature and 70° to 88° C. pot temperature on a one foot Vigreaux column. The distillation residue was stirred with 300 ml. of water, extracted with 150 ml. of hexane and the phases separated. The aqueous phase was then extracted with 50 ml. of hexane and the combined organic phases distilled with 10 g. Primol 355 and 0.1 g. Ionox 220 added to the pot. The distillation parameters were: 30 to 39 mm. Hg, 78° to 115° C. head temperature and 110° to 138° C. pot temperature to recover unreacted methyl heptenone (total of 45.7 g.) and 28 to 30 mm. Hg, 115° to 141° C. head temperature and 138° to 203° C. pot temperature to recover nitrile admixed with propionamide - total of 38 g. mixed C-11 nitrile isomers. The C-11 nitrile-containing fractions were taken up in hexane and washed with water to remove residual propionamide. The washed fractions were then combined with 5 g. Primol 355 and 0.1 g. Ionox 220 and redistilled. The mixed C-11 nitriles distilled at 2.4 to 5 mm. Hg, 84° to 100° C. head temperature and 100° to 103° C. pot temperature on an 18" micro Vigreaux column with reflux head. The nitrile mixture (mainly conjugated isomers as shown by a single IR band at 2220 to 2225 cm$^{-1}$) was interpreted by some perfumers as having a woody, cinnamon fragrance with citrus overtones.

EXAMPLE 4

3,7-Dimethyl-2-Ethyl-2,6-Octadiene Nitrile

Into a 500 ml. flask equipped with a Dean-Stark trap, condensor, mechanical stirrer, thermometer, heating mantle, addition funnel and static nitrogen head was added 0.6 g. of 50% sodium hydride in mineral oil and 70 ml. of benzene followed by a solution of 1.3 g. of n-octanol in 70 ml. of benzene. The flask contents were heated to reflux for one-half hour whereupon 138 g. of butyronitrile were added followed by 63 g. of methyl heptenone. The mixture was held at reflux for a total of 31 hours at 99° to 103° C. with the evolution of 2.6 ml. of water. Solvent was flash evaporated away to give 76.2 g. of crude oil which was combined with 5 g. of Primol 355 and 0.1 g. Ionox 220 prior to flash distillation at between 0.3 and 0.5 mm. Hg, 67° to 137° C. head temperature and 125° to 185° C. pot temperature to give an 11.2 g. fraction containing 86% (9.6 g.) of the desired conjugated nitrile isomers as per GLC.

EXAMPLE 5

Stability Comparisons between Geranonitrile, α-Methyl Geranonitrile and α-Ethyl Geranonitrile Exposed to Heating in the Presence of Air One ml. each of the title nitriles were placed in three separate 11 mm. I.D. test tubes, each containing a ¼" teflon magnetic stirring bar. The test tubes were immersed in a magnetically stirred oil bath, held at 100° C., such that all three test tubes were stirred at the same rate and exposed open to air. After two days, the samples were cooled and compared by GLC to the responses of the original untreated nitriles. GLC conditions: 6' × ¼" stainless steel column packed with 20% Carbowax 20 m on Chromasorb W, He flow ~60 ml./minute, programmed from 135° C. to 220° C. at 4°/minute. The percentages of original nitrile remaining unchanged were geranonitrile 39.6%, α-methyl geranonitrile (product of Example 3) 70.9%, α-ethyl geranonitrile (product of Example 1) 91.8%.

EXAMPLE 6

Stability Comparison Between 3-Methyl-2-Nonene Nitrile and 2,3-Dimethyl-2-Nonene Nitrile upon Acid Treatment A solution was made of 0.2 g. of 3-methyl-2-nonene nitrile, 5.5 g. of isopropyl alcohol and 5.5 g. of 20% aqueous hydrochloric acid. In a similar manner, there was combined 0.2 g. of 2,3-dimethyl-2-nonene nitrile (product of Example 2), 5.5 g. of isopropyl alcohol and 5.5 g. of 20% aqueous hydrochloric acid. The homogeneous samples were then allowed to stand at ambient temperature for 63 hours. The solutions were then neutralized with a 5% stoichiometric excess of 13.7% KOH in methanol and the GLC responses compared to those of the untreated nitriles. GLC conditions: 6' × ¼" stainless steel column packed with 20Carbowax on Chromasorb W, He flow ~60 ml./minute, programmed from 135° C. to 220° C. at 4°/minute. The percentages of original nitrile remaining unchanged were 3-methyl-2-nonene nitrile 36.6% and 2,3-dimethyl-2-nonene nitrile 40.3%.

EXAMPLE 7

2-Cyclohexylidene Heptanonitrile

Into a 25 ml. flask, equipped with magnetic stirrer, heating mantle, condensor, calcium sulfate drying tube, constant temperature controller and thermometer, was charged 0.98 g. of cyclohexanone (0.01 M), 11.1 g. of heptanonitrile (0.10 M) and 0.66 g. of 85% potassium hydroxide flakes. The mixture was heated cooled, 30 ml. of hexane was added, and the mixture washed six times with 30 ml. portions of water and once with saturated brine. The washes were each in succession, cross-extracted with two 15 ml. portions of hexane. The combined organic and hexane phases were dried over anhydrous sodium sulfate and solvent evaporated on a rotary evaporator at ~30 mm. Hg to give 6.7 g. of oil. Gas chromatographic analysis (6' × ¼" column, 20% Carbowax 20 m. on Chromasorb W, programmed 135° C. to 220° C. at 4°/minute, He flow ~60 ml./minute) showed product nitrile peaks at 17.8 minutes (10.3%) and 20.1 minutes (4.1%) with heptanonitrile at 4.3 minutes (85.5%). The product peaks which eluted together at 17.6 minutes on a 20% SE30 column (6' × ¼") under the same operating parameters were trapped out for odor evaluation. An IR spectrum on the trapping of combined isomers showed a nitrile band at 4.5 microns and an olefin band at 6.27 microns. The product was described by perfumers as having an interesting, fruity, floral, salicylate quality.

EXAMPLE 8

2-(4-Methyl Cyclohexylidene) Heptanonitrile

Into a 25 ml. flask, equipped with magnetic stirrer, heating mantle, thermometer, condensor and calcium sulfate drying tube, was charged 1.12 g. of 4-methyl cyclohexanone (0.01 M), 11.1 g. of heptanonitrile, and 0.66 g. of 85% KOH. The mixture was heated to reflux with stirring at about 83° C. for a total of 32 hours. After cooling, 30 ml. of hexane was added and the mixture washed seven times with 30 ml. of H$_2$O, each washing being back-extracted twice with 30 ml. portions of hexane. The combined organic phase and hexane extracts were dried over anhydrous sodium sulfate and the solvent removed by rotary evaporation at about 15 mm. Hg to give 6.3 g. of crude oil. Gas chromatographic analysis (6' × ¼" stainless steel column packed with 20% SE30 on chromasorb W, programmed at 135° to 220° C., 4°/minute, He flow ~60 ml./minute) showed two product peaks at RF 19.0 and 20.2 minutes, which were 6.9% in ratio to heptanonitrile. An IR spectrum of the product peaks, trapped as a group from the gas chromatograph, showed a nitrile band at 4.5 microns and an olefinic band at 6.25 microns. The product was evaluated by perfumers as having a jasminic nitrile type odor with a strong, nerol oxide note.

EXAMPLE 9

2-Pentyl-3-Methyl-2-Nonenyl Nitrile

Into a 25 ml. flask, equipped with magnetic stirrer, thermometer, condensor, heating mantle and calcium sulfate drying tube, was charged 1.28 g. of 2-octanone (0.01 M), 11.1 g. of heptanonitrile (0.1 M) and 0.66 g. of 85% potassium hydroxide flakes. After heating for a total of 45.5 hours at reflux (83° C.), the mixture was cooled. GLC analysis showed the reaction to have gone to ~99% completion. GLC (6' × ¼" stainless steel column packed with 20% Carbowax 20 M on Chromasorb W, He flow ~60 ml./minute, programmed from 135° C. to 220° C. at 4°/minute) analysis showed two product peaks at 11.2 and 13.3 minutes which were 20.8% in ratio to heptanonitrile. Product peaks trapped out together showed a nitrile band at 4.5 microns and an olefin band at 6.25 microns in the IR spectrum. The products, as a mixture, were found by perfumers to have a jasmine, aldehydic, floral character with a mild, woody note.

EXAMPLE 10

3,7-Dimethyl-2-Ethyl-2,6-Octadiene Nitrile

Into a 500 ml. flask, equipped with stirrer, thermometer, condensor, static nitrogen head, heating mantle, additional funnel, and Stark-Dean trap, was charged 0.6 g. of 50% sodium hydride in mineral oil, 1.3 g. of n-octanol and 150 ml. of benzene. After heating the mixture to reflux for one-half hour, there was added 138 g. of butyronitrile, which had been dried over KOH, followed by 63 g. of methyl heptanone. The mixture was held at reflux (100° to 103° C.) for a total of 31 hours. After cooling, the mixture was washed three times with saturated brine, dried over anhydrous sodium sulfate and evaporated on a rotary evaporation unit at ~15 mm. Hg to give 76.2 g. of crude oil. The oil was charged to a micro still with 5 g. of Primol 355 (Esso, high boiling mineral oil) and distilled under the following parameters:

| Time (hr.) | Pot Temp. (°C.) | Head Temp. (°C.) | Vacuum mm. Hg | Fr# | Weight (g.) |
|---|---|---|---|---|---|
|  | 30 | 29 | 81 |  |  |
| 0.28 | 78 | 48 | 81 |  |  |
| 1.12 | 140 | 105 | 78 | 1 | 23.2 |
| 1.32 | 104 | 72 | 17 |  |  |
| 1.42 | 147 | 80 | 17 | 2 | 6.7 |
| 1.50 | 125 | 67 | 3 |  |  |
| 1.72 | 149 | 108 | 0.5 |  |  |
| 2.27 | 185 | 137 | 0.3 | 3 | 11.2 |

Fraction 3 contained 9.6 g. of the title product nitrile = 10.8% conversion.

EXAMPLE 11

2,3-Dimethyl-2-Nonenyl Nitrile

A 20-gallon kettle, equipped with heating jacket, anchor stirrer, and condensor, was charged with 27.5 kg of propionitrile, 2.8 kg of 85% KOH flakes, and 6.4 kg of 2-octanone.

After heating to reflux for a total of 19 hours (95° to 100° C.), 5 kg of Primol 355 was added (mineral oil, Esso), whereupon 15 kg of propionitrile was recovered at 30 mm. Hg at a liquid temperature of 83° to 87° C. and a vapor temperature of 58° to 70° C. over a 2-hour period. The cooled mass was then washed in succession with 10 and then 5 kg portions of water. The remaining oil phase, which weighed 20.1 kg, was charged to a 20-gallon still (all but 2 kg of the crude was charged), along with 7 kg of Primol 355. Fractionation of the crude was carried out under the following parameters on a 6' × 4" Koch Sulzer column:

| Time (hr.) | Pot Temp. (°C.) | Head Temp. (°C.) | Vacuum mm. Hg | Comments |
|---|---|---|---|---|
| 2.18 | 119 | 56 | 3.0 | Fr. 1,¼ gal.,RR 15:2 |
| 3.00 | 120 | 90 | 2.4 | Fr.2,¼ gal.,RR 15:2 |

| Time (hr.) | Pot Temp. (°C.) | Head Temp. (°C.) | Vacuum mm. Hg | Comments |
|---|---|---|---|---|
| 3.62 | 121 | 94 | 2.4 | Fr.3,¼ gal.,RR 15:2 |
| 4.19 | 132 | 98 | 2.4 | Fr.4,½ gal.,RR 15:2 |
| 4.50 | 134 | 98 | 2.4 | Fr.5,½ gal.,RR 15:2 |
| 4.65 | 136 | 98 | 2.4 | Fr.6,½ gal.,RR 10:5 |
| 5.78 | 138 | 98 | 2.4 | Fr.7,1 gal.,RR 5:5 |
| 5.92 | 148 | 98 | 2.4 | Fr.8,1 gal.,RR 5:5 |
| 5.95 | 154 | 84 | 2.1 | Fr.9,1 gal.,RR 5:5 |

Fractions 2 through 4 were bulked as 2-octanone for recycle (780 g. of 84% starting material), and fractions 5 through 9 were bulked as product (2.8 kg). The bulked product was then washed with 1 kg of $H_2SO_4$ solution to remove traces of propionamide, followed by water-/washing, and then washing with 2 kg of 5% $NaHCO_3$ to pH 7. After drying over Mg $SO_4$, followed by filtration through diatomaceous earth to clarify, the material was submitted for organoleptic evaluation, whereupon it was determined that the odor was off-quality, most likely due to C-11 carboxylic acid impurities (2.75 kg of oil recovered). The oil was then washed with 20% sodium hydroxide solution, redried over anhydrous sodium sulfate, and refiltered through diatomaceous earth to give good organoleptic quality product.

EXAMPLE 12

2,3,7-Trimethyl-2,6-Octadienyl Nitrile

A flask, equipped with a static nitrogen head, stirrer, reflux condensor, and thermometer, was charged with 252 g. of methyl heptenone, 1100 g. of propionitrile, and 132 g. of 85% KOH flakes. The mixture was held at reflux, with stirring (103° to 105° C.) for a total of 22.5 hours. After cooling, excess propionitrile was recovered at 100 mm Hg, temperature range 45° to 75° C. in the pot. Water was added (500 ml.), along with 250 ml. of hexane. After stirring, the water layer was separated, the organic phase was again washed twice with 250 ml. portions of water. After drying over anhydrous sodium sulfate, the organic phase was fractionated on a 13 mm. × 4' spinning band column under the following parameters:

| Time (hr.) | Pot Temp. (°C.) | Vapor Temp. (°C.) | Vacuum mm. Hg | Fraction | Weight (g.) | Comments |
|---|---|---|---|---|---|---|
| 0 | 100 | | | | | RR 15:2 |
| 0.33 | 97 | 90 | 4.0 | 1 | 9.5 | |
| 0.56 | 98 | 92 | 4.0 | 2 | 14.5 | RR 5:5 |
| 0.74 | 101 | 93 | 4.0 | 3 | 27.0 | |
| 0.84 | 102 | 93 | 4.0 | 4 | 27.5 | |
| 0.94 | 102 | 93 | 4.0 | 5 | 26.5 | |
| 1.11 | 109 | 93 | 4.0 | 6 | 27.5 | |
| 1.24 | 119 | 94 | 4.0 | 7 | 26.0 | |
| 1.41 | 137 | 96 | 4.0 | 8 | 19.0 | Off |

Fractions 2 through 8 bulked as product, 168 g.

EXAMPLE 13

2-Ethyl-3,7-Dimethyl-2,6-Octadiene Nitrile

Into a 3-liter flask, equipped with mechanical stirrer, reflux condensor, thermometer, and static nitrogen head, was charged 252 g. of methyl heptenone, 1380 g. of butyronitrile and 132 g. of 85% KOH. The mixture was heated at between 91° and 121° C., with stirring, for a total of 23 hours, cooled, and excess nitrile removed under steam heat at 100 mm. Hg for one hour at 90° to 95° C. in the pot. After cooling, the crude oil was washed once with 500 g. of water, after adding 250 ml. of hexane. The organic phase was separated and washed in succession with 1000 ml. $H_2O$, 500 ml. $H_2O$, and 500 ml. $H_2O$. The organic phase was then fractionated on a 13 mm. × 4' spinning band column, under the following parameters, to recover product:

| Time (hr.) | Pot Temp. (°C.) | Head Temp. (°C.) | Vacuum mm Hg | Fraction | Weight (g.) | Comments |
|---|---|---|---|---|---|---|
| 0 | 25 | 25 | 3 | | | RR 15:2 |
| 2.0 | 132 | 78 | 3 | 1 | 25 | |
| 2.2 | 145 | 117 | 3 | 2 | 27.5 | |
| 2.3 | 152 | 117 | 3 | 3 | 10.5 | $ND_{23}$ 1.4708 |
| 2.5 | 162 | 117 | 3 | 4 | 12.0 | |
| 2.6 | 170 | 109 | 3 | 5 | 15.0 | RR 10:5 |
| 2.8 | 188 | 63 | 3 | 6 | 7.0 | |
| | | | | | residue —15.5 | |

Fractions 3 to 5, when bulked, gave acceptable odor quality product.

EXAMPLES 14 THROUGH 32

Following the general procedure as described in Examples 1 through 4, 7 through 9, and 11 through 13, the ketones set forth in Table I were also reacted, under the conditions set forth in the table, i.e., 10 M of nitrile reacted with 1 M of ketone in the presence of 1 M KOH at 90° to 100° C. for 19 hours with the usual workup:

Table I

| Example No. | Ketone | Nitrile | Conversion (%) | Yield (%) | Odor Type |
|---|---|---|---|---|---|
| 14 | Methyl isobutyl ketone | Butyronitrile | ~8 | | |
| 15 | 2-Pentanone | Butyronitrile | ~8 | | Lovage |
| 16 | 2-Octanone | Butyronitrile | ~2 | 5.3 | Anis, lovage, heliotropine |
| 17 | 2-Pentanone | Valeronitrile | 2.5 | | |
| 18 | 3-Heptanone | Butyronitrile | ~4 | ~9.5 | Lovage, butyric |
| 19 | 2-Hexanone | Propionitrile | 32.8 | 54 | Waxy, terpenic, cumin |
| 20 | β-Decalone | Propionitrile | 66.2 | 75.5 | Sweet, rosy, coumarinic |
| 21 | 4-Methyl cyclohexanone | Butyronitrile | 52.8 | 58 | Resinous, myrrh, celery, tobacco |
| 22 | 4-Methyl cyclohexanone | Valeronitrile | 42.9 | 50.1 | Similar to Example 21, + soapy, jasmone |
| 23 | 4-t-Butyl cyclohexanone | Propionitrile | 77.5 | 78 | Bready, coconut, musty |
| 24 | 3-Heptanone | Propionitrile | 19 | 20 jasmone, lactonic | Strong, floral, almond, |

Table I-continued

| Example No. | Ketone | Nitrile | Conversion (%) | Yield (%) | Odor Type |
|---|---|---|---|---|---|
| 25 | Cyclohexanone | Propionitrile | 29.6 | 37.4 | Strong, cinnamic, almond |
| 26 | 6,9-Dimethyl-5-decen-2-one | Propionitrile | 48.8 | 51.8 | Fatty, lemony, floral, green water |
| 27 | 4-Methyl cyclohexanone | Propionitrile | 75 | 79.4 | Fruity, rosy, ylang benzoate |
| 28 | 2-Dodecanone | Propionitrile | 49 | 51.7 | Watery, aldehydic |
| 29 | 3,3,5-Trimethyl cyclo- | Propionitrile | 44.2 | 66.3 | Paatchone, soapy, woody |
| 30 | Dihydro α-ionone | Propionitrile | 41.6 | 41.6 | Mixture of α, β, and γ isomers, woody, fatty, hairy, indolic |
| 31 | Carvomethanone | Propionitrile | 25.6 | 63.8 | Woody |
| 32 | Cyclododecanone | Propionitrile | 14.6 | 83.3 | Earthy, musky, musty, woody |

EXAMPLE 33

2,3-Dimethyl-2-Nonene Nitrile

Into a 100 ml. flask, equipped with magnetic stirrer, thermometer, condensor and static nitrogen head, was placed 23.6 g. of 2-octanone (0.18 m), 22 g. of propionitrile (0.4 m), 7 g. of Ca(OH)$_2$ (0.09 m), 7 g. of CaO (0.12 m), and 0.6 g. of 25% tetramethyl ammonium hydroxide in water. The solution was held at reflux for 64 hours, whereupon a gas chromatographic analysis of a sample of the reaction mixture showed 10.7% conversion of the ketone to the product nitrile.

EXAMPLE 34

Stability Comparisons between Geranonitrile, α-Methyl Geranonitrile and α-Ethyl Geranonitrile upon Ultraviolet Irradiation One gram samples of geranonitrile, α-methyl geranonitrile and α-ethyl geranonitrile were placed separately into 12 mm. I.D. Pyrex test tubes. The samples were irradiated by placing a longwave ultraviolet lamp over the test tube openings, such that the samples were exposed directly to the light (G.E. F15T8-BL, 118 volt, 15 watt, 60 cycle lamp employing a long-wave U.V. bulb, Lux-O-Fluorescent, from Luxo lamp Cor.). After 12 days of irradiation the samples were analyzed by gas chromatography - 6 foot by ¼ inch stainless steel column packed with 20% Carbowax 20M, He flow ~60 ml./min., programmed from 135° to 220° C. at 8°/minute. The percentages of original nitrile remaining were geranonitrile 76.4%, α-methyl geranonitrile 93.4%, and α-ethyl geranonitrile 83.4%, indicating that the α,β-dialkyl substituted materials are more stable than the known geranonitrile.

EXAMPLE 35

2,3-Dimethyl-2-Nonene Nitrile

Into a 100 ml. flask, equipped with a magnetic stirrer, thermometer, condensor, and static nitrogen head, was placed 13.6 g. of 2-octanone, 11 g. of propionitrile, 61 g. of calcium oxide and 0.3 g. of 25% tetramethyl ammonium hydroxide in water. The mixture was held at reflux (103° C.) for 16 hours at which time gas chromatographic analysis showed 7% product nitrile relative to starting ketone.

EXAMPLE 36

| Jasmine Complex | |
|---|---|
| Diethyl Phthalate | 15 |
| 2,3-Dimethyl-2-none nitrile | 20 |
| Indolene (8,8-bis(3H-indol-3-yl)-2,6-dimethyl-2-octanol | 15 |
| Delta decalactone | 5 |
| Methyl cinnamate | 2 |
| Para cresyl acetate | 2 |
| Para cresyl isobutyrate | 1 |
| Geranyl linalool | 90 |
| Terpineol | 90 |
| Isophytol | 380 |
| Benzyl acetate | 335 |
| Tepyl acetate (U.O.P. Chem. Co. Register) | 35 |
| Coumarin | 10 |
| | 1000 |

EXAMPLE 37

| Citrus Cologne | |
|---|---|
| Diethyl phthalate | 5 |
| 2,3,7-Trimethyl-2,6-Octadiene nitrile | 20 |
| Mousse de Chene | 5 |
| Linalyl isobutyrate | 5 |
| Cuminyl alcohol | 40 |
| Citral | 80 |
| Tangerine oil Florida | 60 |
| Octacetal (IFF Register) | 2 |
| Undecylic aldehyde | 3 |
| Lemon oil, California | 100 |
| Terpinyl acetate | 150 |
| Citronellol | 500 |
| Coumarin | 38 |
| | 1000 |

What I claim and desire to protect by Letters Patent is:

1. A method of preparing an aliphatic nitrile having the formula

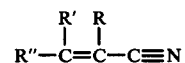

wherein R is an alkyl or alkylene radical of about 1 to 15 carbon atoms free of unsaturation in conjugated relationship with the nitrile or the olefinic unsaturation, and R' and R" are the same or different radicals meeting the description of R; or R' and R" taken together represent a cycloaliphatic radical having 6 to 15 carbon atoms, which method comprises reacting a ketone of the formula

with a nitrile of the formula R—CH$_2$-C≡N in the presence of about 0.1 to 10 moles per mole of ketone of a basic catalyst selected from the class consisting of alkali metal hydroxides, alkali earth metal hydroxides, and quaternary ammonium hydroxides.

2. The method of claim 1 wherein the basic catalyst is an alkali metal hydroxide.

3. The method of claim 2 wherein the basic catalyst is potassium hydroxide.

4. The method of claim 3 wherein the potassium hydroxide is present in the amount of about 0.1 to 5 moles per mole of ketone.

5. The method of claim 2 wherein the basic catalyst is a quaternary ammonium hydroxide.

6. The method of claim 1 wherein the basic catalyst is an alkaline earth metal hydroxide.

7. A method of preparing an aliphatic nitrile having the formula

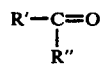

wherein R is an alkyl or alkylene radical of about 1–15 carbon atoms free of unsaturation in conjugated relationship with the nitrile or the olefinic unsaturation, and R' and R" are the same or different radicals meeting the description of R or R' and R" taken together represent a cycloaliphatic radical having 6–15 carbon atoms, which method comprises reacting a ketone of the formula $$R'-C=O$$
$$|$$
$$R''$$

with a nitrile of the formula R—CH$_2$C≡N in the presence of a phase transfer agent and about 0.1–10 moles per mole of ketone of calcium hydroxide.

8. The method of claim 7 wherein the reaction is carried out in the presence of calcium hydroxide as a water trapping agent.

9. The method of claim 8 wherein the phase transfer agent is tetramethyl ammonium hydroxide.

* * * * *